United States Patent
Yazdani et al.

(10) Patent No.: US 9,631,206 B2
(45) Date of Patent: Apr. 25, 2017

(54) MODIFIED BACTERIA FOR THE PRODUCTION OF BIOALCOHOL

(71) Applicants: DEPARTMENT OF BIOTECHNOLOGY MINISTRY OF SCIENCE & TECHNOLOGY, New Delhi (IN); INTERNATIONAL CENTRE FOR GENETIC ENGINEERING AND BIOTECHNOLOGY (ICGEB), New Delhi (IN)

(72) Inventors: Syed Shams Yazdani, New Delhi (IN); Neha Munjal, New Delhi (IN); Anu Jose Mattam, New Delhi (IN)

(73) Assignees: DEPARTMENT OF BIOTECHNOLOGY MINISTRY OF SCIENCE & TECHNOLOGY, New Delhi (IN); INTERNATIONAL CENTRE FOR GENETIC ENGINEERING AND BIOTECHNOLOGY (ICGEB), New Delhi (IN)

( * ) Notice: Subject to any disclaimer, the term of this patent is extended or adjusted under 35 U.S.C. 154(b) by 107 days.

(21) Appl. No.: 14/424,037

(22) PCT Filed: Aug. 30, 2013

(86) PCT No.: PCT/IN2013/000535
§ 371 (c)(1),
(2) Date: Feb. 26, 2015

(87) PCT Pub. No.: WO2014/033759
PCT Pub. Date: Mar. 6, 2014

(65) Prior Publication Data
US 2015/0299736 A1    Oct. 22, 2015

(30) Foreign Application Priority Data
Aug. 30, 2012  (IN) .......................... 2696/DEL/2012

(51) Int. Cl.
| | | |
|---|---|---|
| C12P 7/04 | (2006.01) | |
| C12P 7/06 | (2006.01) | |
| C12P 19/02 | (2006.01) | |
| C12P 19/14 | (2006.01) | |
| C12P 7/10 | (2006.01) | |

(52) U.S. Cl.
CPC ................. *C12P 7/065* (2013.01); *C12P 7/10* (2013.01); *C12P 19/02* (2013.01); *C12P 19/14* (2013.01); *C12P 2203/00* (2013.01); *Y02E 50/16* (2013.01); *Y02E 50/17* (2013.01)

(58) Field of Classification Search
CPC ..................................... C12P 7/04; C12P 7/06
See application file for complete search history.

(56) References Cited

U.S. PATENT DOCUMENTS

2009/0082600 A1*  3/2009  Zhou ...................... C12N 15/52
                                                                    568/840

OTHER PUBLICATIONS

Manow et al., J. Ind. Microbiol. Biotechnol., 2012, 39, 977-985.*

* cited by examiner

*Primary Examiner* — Maryam Monshipouri
(74) *Attorney, Agent, or Firm* — Mark M. Friedman

(57) ABSTRACT

The present invention provides a modified bacterial strain capable of fermenting both hexose and pentose sugars for production of bioalcohol wherein a promoter of pyruvate dehydrogenase operon (PDH) is replaced with a promoter of a gene that is expressed under anaerobic conditions. The present invention further provides a method of obtaining modified bacterial strain capable of fermenting both hexose and pentose sugar for production of bioalcohol. The present invention also provides a method of fermenting lignocellulosic biomass having hexose and pentose sugar using the modified bacteria for production of biomass.

7 Claims, 11 Drawing Sheets

(A)

(B)

(A)

(B)

(A)

(B)

(A)

(B)

(A)

(B)

(A)

(B)

SEQUENCE LISTING

<160> NUMBER OF SEQ ID NOS: 22

<210> SEQ ID NO 1

-continued

<211> LENGTH: 31
<212> TYPE: DNA
<213> ORGANISM: E. coli

<400> SEQUENCE: 1
ggagagaatt cgtgtaggct ggagctgctt c                          31

<210> SEQ ID NO 2
<211> LENGTH: 30
<212> TYPE: DNA
<213> ORGANISM: E. coli

<400> SEQUENCE: 2
ggagaggatc catatgaata tcctccttag                            30

<210> SEQ ID NO 3
<211> LENGTH: 27
<212> TYPE: DNA
<213> ORGANISM: E. coli

<400> SEQUENCE: 3
tcgggatccg caagctgaca atctccc                               27

<210> SEQ ID NO 4
<211> LENGTH: 32
<212> TYPE: DNA
<213> ORGANISM: E. coli

<400> SEQUENCE: 4
actcaagctt aagactttct ccagtgatgt tg                         32

<210> SEQ ID NO 5
<211> LENGTH: 28
<212> TYPE: DNA
<213> ORGANISM: E. coli

<400> SEQUENCE: 5
tgcggatcca tcaaacagcg gtgggcag                              28

<210> SEQ ID NO 6
<211> LENGTH: 29
<212> TYPE: DNA
<213> ORGANISM: E. coli

<400> SEQUENCE: 6
cccaagcttg acattcctcc agattgttt                             29

<210> SEQ ID NO 7
<211> LENGTH: 34
<212> TYPE: DNA
<213> ORGANISM: E. coli

<400> SEQUENCE: 7
tcgggatcca accatgcgag ttacgggcct ataa                       34

<210> SEQ ID NO 8
<211> LENGTH: 34
<212> TYPE: DNA
<213> ORGANISM: E. coli

<400> SEQUENCE: 8
cccaagcttg tgcctgtgcc agtggttgct gtga                       34

```
<210> SEQ ID NO 9
<211> LENGTH: 29
<212> TYPE: DNA
<213> ORGANISM: E. coli

<400> SEQUENCE: 9
cgcggatccc cggataatgt tagccataa                                    29

<210> SEQ ID NO 10
<211> LENGTH: 30
<212> TYPE: DNA
<213> ORGANISM: E. coli

<400> SEQUENCE: 10
cccaagctta atgctctcct gataatgtta                                   30

<210> SEQ ID NO 11
<211> LENGTH: 31
<212> TYPE: DNA
<213> ORGANISM: E. coli

<400> SEQUENCE: 11
cgcggatccg attctaacaa aacattaaca c                                 31

<210> SEQ ID NO 12
<211> LENGTH: 29
<212> TYPE: DNA
<213> ORGANISM: E. coli

<400> SEQUENCE: 12
cccaagctta tattccacca gctatttgt                                    29

<210> SEQ ID NO 13
<211> LENGTH: 65
<212> TYPE: DNA
<213> ORGANISM: E. coli

<400> SEQUENCE: 13
ctcctttcct acgtaaagtc tacatttgtg catagttaca actttgtgta ggctggagct    60
gcttc                                                              65

<210> SEQ ID NO 14
<211> LENGTH: 67
<212> TYPE: DNA
<213> ORGANISM: E. coli

<400> SEQUENCE: 14
gcgagtttcg atcggatcca cgtcatttgg gaaacgttct gacataagac tttctccagt    60
gatgttg                                                            67

<210> SEQ ID NO 15
<211> LENGTH: 65
<212> TYPE: DNA
<213> ORGANISM: E. coli

<400> SEQUENCE: 15
gcgagtttcg atcggatcca cgtcatttgg gaaacgttct gacataatgc tctcctgata    60
atgtt                                                              65

<210> SEQ ID NO 16
<211> LENGTH: 65
<212> TYPE: DNA
```

<213> ORGANISM: E. coli

<400> SEQUENCE: 16
gcgagtttcg atcggatcca cgtcatttgg gaaacgttct gacatatatt ccaccagcta    60
tttgt    65

<210> SEQ ID NO 17
<211> LENGTH: 65
<212> TYPE: DNA
<213> ORGANISM: E. coli

<400> SEQUENCE: 17
gcgagtttcg atcggatcca cgtcatttgg gaaacgttct gacatgacat tcctccagat    60
tgttt    65

<210> SEQ ID NO 18
<211> LENGTH: 81
<212> TYPE: DNA
<213> ORGANISM: E. coli

<400> SEQUENCE: 18
gcgagtttcg atcggatcca cgtcatttgg gaaacgttct gacatgtaac acctacctte    60 tgttgctgtg atatagaaga c    81

<210> SEQ ID NO 19
<211> LENGTH: 21
<212> TYPE: DNA
<213> ORGANISM: E. coli

<400> SEQUENCE: 19
tgcatggttg aagatgagtt g    21

<210> SEQ ID NO 20
<211> LENGTH: 21
<212> TYPE: DNA
<213> ORGANISM: E. coli

<400> SEQUENCE: 20
tgatgtagtt gctgatacct g    21

<210> SEQ ID NO 21
<211> LENGTH: 33
<212> TYPE: DNA
<213> ORGANISM: E. coli

<400> SEQUENCE: 21
gatcggatcc atgtcgagta agttagtact ggt    33

<210> SEQ ID NO 22
<211> LENGTH: 29
<212> TYPE: DNA
<213> ORGANISM: E. coli

<400> SEQUENCE: 22
tcgagtcgac tcaggcagtc aggcggctc    29

MODIFIED BACTERIA FOR THE PRODUCTION OF BIOALCOHOL

REFERENCE TO A SEQUENCE LISTING

This application contains a sequence listing, provided as a text file named "Sequence Listing.txt", file created on Jun. 17, 2015 and containing 4.00 KiloBytes (KB), as required under 37 C.F.R. 1.821(c), and is herein incorporated by reference in its entirety, as required under 37 C.F.R. 1.52(e)(5).

FIELD OF THE INVENTION

The present invention relates to the field of bioalcohol production by engineering native pathways to enhance production of bioalcohols in bacteria. More particularly the present invention provides modified bacteria which are able to ferment both hexose and pentose sugar, method of obtaining such modified bacteria and method fermenting lignocellulosic biomass having hexose and pentose sugar.

BACKGROUND OF THE INVENTION

People are largely dependent upon fossil fuels for fulfilling our energy requirement. Bioalcohol, in particular ethanol is an attractive alternate transportation fuel to replace at least a part of petroleum. Fuels from renewable sources like agricultural and forest residues hold promise in reducing their dependence on fossil fuel without competing with food. The agricultural and forestry waste mostly consist of lignocellulose, which is made-up of highly structured cellulose surrounded by hemicellulose and lignin. In principle, it is possible to breakdown lignocellulose into the monosaccharides and ferment them into ethanol. However, cost associated with this process is a major hurdle in terms of commercial application. One of the key advancement in the economy of ethanol production from lignocellulosic biomass will be to efficiently ferment both hexose and pentose sugars released after hydrolysis of lignocellulose into ethanol.

Unfortunately, the conventional microorganisms used for ethanol fermentation, e.g., *Saccharomyces cerevisiae* and *Zymomonas mobilis*, do not have the capability to utilize pentose sugars, Attempts have been made to transfer genes for pentose degradation pathway from other organisms into *S. cerevisiae* and *Z. mobilis*. However, the disadvantages associated with foreign gene expression at large scale like instability, toxicity, containment, etc., prevent its wide usage. *Escherichia coli*, on the other hand, has the ability to ferment both hexose and pentose sugars and is being used to produce ethanol by various genetic manipulation The genetic manipulation of *E. coli* that does not involve introduction of foreign gene has been attempted with some successes and these technologies have advantages in the long-term genetic stability of the engineered strain.

Under anaerobic condition, *E. coli* produces ethanol through a pathway that involves pyruvate formate lyase (PFL), which converts pyruvate into acetyl CoA and formate (FIG. 1). However, this pathway is not redox balanced because in the process of metabolizing one mole of glucose into ethanol, four moles of NADH are consumed while only two moles of NADH are produced. This redox imbalance would negatively impact the yield of ethanol. However, there is an alternate pathway exists where converting glucose into ethanol or butanol is a redox balance process. Here pyruvate in converted into acetyl CoA and $CO_2$ via pyruvate dehydrogenase complex (PDH) and in the process one molecule of NADH is produced. However, expression of PDH is repressed under anaerobic condition and remains active in the aerobically growing cells. To activate the expression of PDH under anaerobic condition, the promoter of PDH should be replaced with the one that is highly active under anaerobic condition. Attempts of replacing the PDH promoter with the PFL promoter have not been found to be very successful, as despite showing the enhanced expression of PDH under anaerobic condition and increased the yield of ethanol, the net ethanol productivity was low.

Thus, there is a need for a modified bacterial strain with genetic alterations that can ferment both hexose and pentose sugars in order to produce bioalcohol such as ethanol with high productivity.

SUMMARY OF THE INVENTION

Accordingly, in general aspect the present invention provides engineering of native pathways in bacteria to enhance production of bioalcohols by fermentation of hexose and pentose sugar.

In one of the aspect the present invention provides a modified bacterial strain capable of fermenting both hexose and pentose sugars for production of bloalcohol.

In one embodiment the present invention provides a modified bacterial strain capable of fermenting both hexose and pentose sugars for production of bioethanol from lignocellulosic biomass.

In one embodiment the present invention provides a modified bacterial strain wherein a promoter of one gene may be replaced with a promoter of another gene for expression under anaerobic conditions.

In one embodiment the present invention provides a modified *E. coli* strain wherein the *E. coli* is modified by replacing a promoter of one gene with a promoter of another gene for expression under anaerobic conditions.

In one embodiment the present invention provides a modified *E. coli* strain wherein the promoter of pyruvate dehydrogenase operon (PDH) is replaced with a promoter of a gene that is expressed under anaerobic conditions.

In one embodiment the present invention provides a modified *E. coli* strain wherein the promoter of pyruvate dehydrogenase operon (PDH) is replaced with a promoter of a gene selected from frdA, ldhA, pflB, adhE and gapA.

In one embodiment the present invention provides a modified bacterial strain wherein the promoter of pyruvate dehydrogenase operon (PDH) is replaced with a gapA promoter.

In one embodiment the present invention provides a modified *E. coli* strain wherein the genes responsible for competing products consisting of lactate, succinate, acetate and formate are deleted.

In one embodiment the present invention provides a modified bacterial strain wherein basal level expression of one or more genes of the competing product may be reintroduced.

In one aspect the present invention provides a method of obtaining the modified bacterial strain capable of fermenting both hexose and pentose sugars for production of bioalcohol.

In one embodiment the present invention provides a method of obtaining a modified *Escherichia coli* strain wherein the method comprises the steps of:
 a. replacing the promoter of pyruvate dehydrogenase operon (PDH) with a promoter of a gene that is expressed at high level under anaerobic conditions;

b. introducing mutations by deleting genes responsible for competing products that is lactate, succinate, acetate and formate and c. reintroducing basal level expression of gene encoding acetate kinase.

In one embodiment the present invention provides a method of obtaining the modified bacterial strain wherein the promoter of pyruvate dehydrogenase operon (PDH) is replaced with a promoter of a gene selected from frdA, ldhA, pflB, adhE and gapA.

In one embodiment the present invention provides a method of obtaining the modified bacterial strain wherein the promoter of PDH is replaced with a promoter of a gapA gene.

In one embodiment the present invention provides a method of fermenting hexose and/or pentose sugars utilizing the modified E. coli strain for the production of bioalcohol.

In one embodiment the present inventions provides a method of fermenting lignocellulosic biomass comprising hexose and pentose sugars by using the modified bacterial strain.

In some embodiments of the invention, the method of fermenting hexose and pentose sugars comprised in lignocellulosic biomass by using the modified bacterial strain for the production of bioalcohol under aerobic, microaerobic and/or anaerobic conditions.

In one embodiment the present invention provides a method of fermenting lignocellulosic biomass with a modified Escherichia coli strain wherein the method comprises the steps of:

hydrolyzing the lignocellulosic biomass comprising hexose and pentose sugars;

mixing the modified Escherichia coli strain with hydrolyzed lignocellulosic biomass comprising hexose and pentose sugars;

allowing fermentation of the mixture to be carried out in microaerobic conditions.

DETAILED DESCRIPTION OF THE INVENTION

Figure 1:
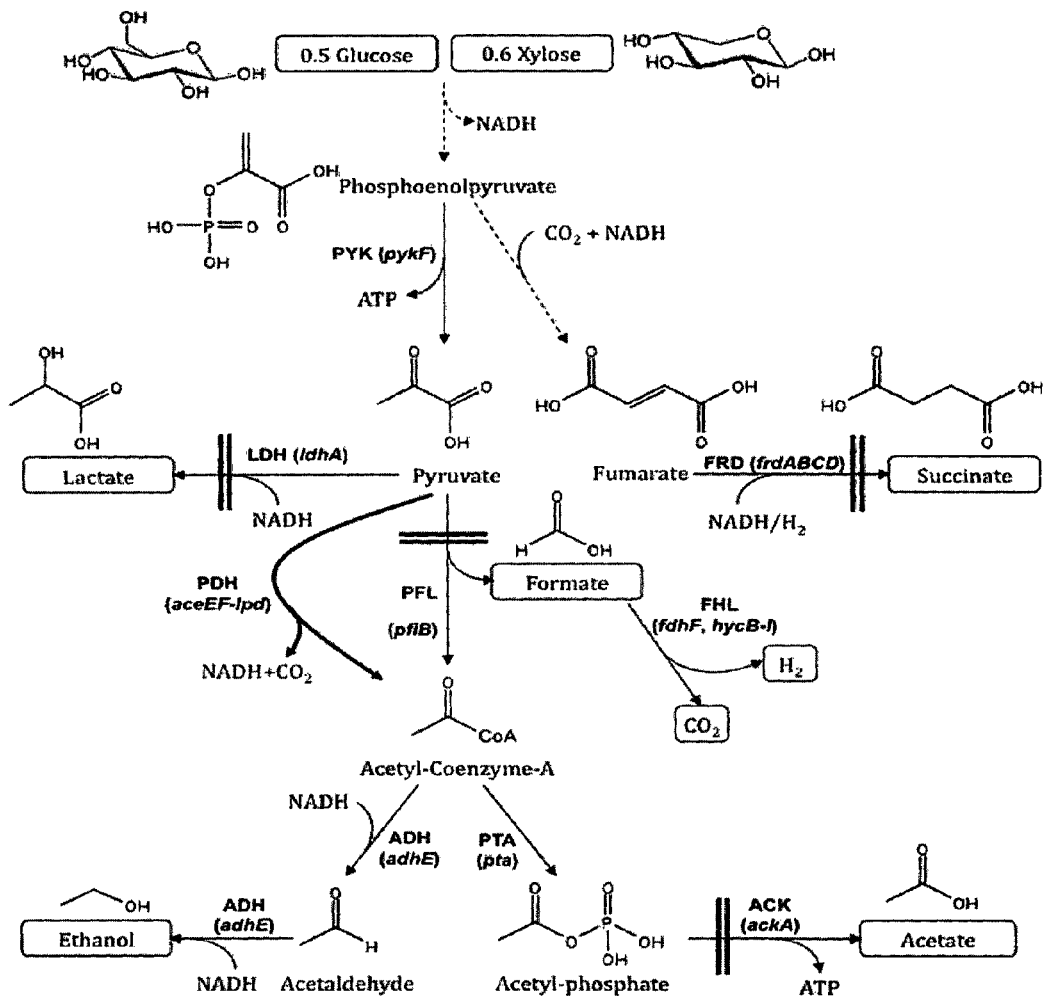
FIG. 1 is a graph showing metabolic pathways of E. coli functional under anaerobic conditions during glucose and xylose fermentation.

Although the present invention has been explained in relation to its embodiments, it is to be understood that many other possible modifications and variations can be made without departing from the spirit and scope of the invention as hereinafter disclosed. Furthermore, the description is for the purpose of illustration only and it is to be understood that the terminology used is intended to be in the nature of description rather than of limitation and hence, the invention may be practiced otherwise than as specifically described.

The present invention is directed to engineering of the native pathways in bacteria to enhance production of bioalcohol.

The present invention provides a modified bacterial strain capable of fermenting both hexose and pentose sugars for production of bioalcohol. The present invention in additional aspect provides method of obtaining modified bacterial strain capable of fermenting both hexose and pentose sugar for production of bioalcohol. The present invention further provides a method of fermenting lignocellulosic biomass having hexose and pentose sugar using the modified bacteria for production of bioalcohol.

In one embodiment the present invention provides a modified bacterial strain capable of fermenting both hexose and pentose sugars for production of bioethanol from lignocellulosic biomass.

In some embodiments the present invention provides a modified bacterial strain wherein a promoter of one gene is replaced with a promoter of another gene for expression under anaerobic conditions. In some embodiments the invention provides the modified bacterial strain that does not involve the introduction of foreign genes.

In one embodiment, the modified bacterial strain is *Escherichia coli*.

In one embodiment, the modified bacterial strain is *Escherichia coli* MTCC 5852.

In one embodiment, the bioalcohol that is produced by the modified *E. coli* strain is ethanol.

In some embodiments, the hexose sugar that the modified *E. coli* strain can ferment can be selected from glucose, galactose, allose, altrose, mannose, gulose, idose and talose. In one embodiment, the hexose sugar that the modified *E. coli* strain can ferment can be glucose and/or galactose. In one embodiment, the hexose sugar that the modified *E. coli* strain can ferment is glucose.

In some embodiments, the pentose sugar that the modified *E. coli* strain can ferment can be selected from xylose, arabinose, ribose, lyxose, ribulose and xylulose. In one embodiment, the pentose sugar that the modified *E. coli* strain can ferment can be xylose and/or arabinose. In one embodiment, the pentose sugar that the modified *E. coli* strain can ferment can be xylose.

In some embodiments, the promoter of an operon in the modified *E. coli* strain is replaced with a promoter of a gene that can be expressed at high level under anaerobic conditions.

In one embodiment, the promoter of a gene that can be replaced in the modified *E. coli* strain may be pyruvate dehydrogenase operon (PDH).

In one embodiment of the invention, the promoter of pyruvate dehydrogenase operon (PDH) in the modified *E. coli* strain can be replaced with a promoter of a gene that can be expressed at high level under anaerobic conditions.

In some embodiments a promoter of a gene that can replace the promoter of native gene in the *E. coli* and that be expressed at high level under anaerobic conditions can be selected from at least one selected from but not limiting to frdA, ldhA, pflB, adhE and gapA.

In one embodiment, the promoter of an operon in the modified *E. coli* strain that replaces the promoter of native gene and such replaced promoter which can be expressed at high levels under anaerobic conditions is gapA.

In one embodiment of the invention, the promoter of pyruvate dehydrogenase operon (PDH) in the modified *E. coli* strain is replaced with the promoter of the gapA gene.

In some embodiments, the modified *E. coli* strain includes delete mutations in the gene of competing products.

In one embodiment the present invention the modified *E. coli* comprises deletion of genes responsible for competing products that is lactate, succinate, acetate and formate.

In one embodiment, the modified *E. coli* comprises deletion of the gene of competing product lactate that is Lactate dehydrogenase (ldhA).

In some embodiments, the modified *E. coli* comprises deletion of the genes of competing product acetate that may be selected from Phosphotransacetylase (pta), Acetate kinase (ack).

In one embodiment, the modified *E. coli* comprises deletion of the gene of competing product acetate that is Acetate kinase (ack). The acetate Acetate kinase (ack) gene may be Acetate kinase A(ack A) or Acetate kinase B (ackB).

In one embodiment, the modified *E. coli* comprises deletion of the genes of competing product succinate that can be selected from Fumarate Reductase A (frdA), Fumarate Reductase B (frdB), Fumarate Reductase C (frdC), Fumarate Reductase D (frdD), Succinyl coA synthetase and Isocitrate lyase.

In one embodiment, the modified *E. coli* comprises deletion of the gene of competing product succinate that is Fumarate Reductase A (frdA).

In one embodiment, the modified *E. coli* comprises deletion of the gene of competing product formate that can be selected from Pyruvate formate lyase A (pflA), Pyruvate formate lyase B (pflB), Pyruvate formate lyase C (pflC) and Pyruvate formate lyase D (pflD).

In one embodiment, the modified *E. coli* comprises deletion of the gene of competing product formate that is Pyruvate formate lyase B (pflB).

In some embodiments in the modified *E. coli* the basal level expression of one or more genes of the competing product may be reintroduced.

In one embodiment in the modified *E. coli* strain the basal level expression of acetate kinase (ack) is reintroduced.

In one embodiment of the present invention provides the modified *E. coli* strain comprising of the promoter of pyruvate dehydrogenase operon (PDH) replaced with a promoter of the gapA gene, delete mutations of genes responsible for competing products that is lactate, succinate, acetate and formate and reintroduction of basal level expression of acetate kinase.

In some embodiments the present invention provides a method of obtaining the modified bacterial strain that can ferment both hexose and pentose sugars for enhanced production of bioalcohol.

In one embodiment, the present invention provides a method of obtaining the modified *E. coli* strain wherein the modified *E. coli* strain is capable of fermenting hexose and pentose sugars comprised in lignocellulosic biomass for enhanced production of bioalcohol.

In some embodiments of the invention, the method for obtaining the modified *E. coli* strain comprises of replacing the promoter of an operon in the modified *E. coli* strain with a promoter of a gene that can be expressed at high level under anaerobic conditions.

In some embodiments, the method for obtaining the modified *E. coli* strain comprises replacing the promoter of an operon with a promoter of a gene that can be expressed at high level under anaerobic conditions.

In one embodiment, the method for obtaining the modified *E. coli* strain comprises replacing of the promoter of pyruvate dehydrogenase operon (PDH).

In some embodiments, the method for obtaining the modified *E. coli* strain comprises replacing a promoter of PDH in the *E. coli* and with a promoter that can be expressed at high level under anaerobic conditions, wherein the promoter replacing the PDH promoter can be at least one selected from but not limiting to frdA, ldhA, pflB, adhE and gapA.

In one embodiment, the method for obtaining the modified *E. coli* strain comprises replacing the promoter of PDH with gapA promoter.

In some embodiments, the method for obtaining the modified *E. coli* strain comprises deleting genes responsible for competing products that is lactate, succinate, acetate and formate.

In one embodiment, the method for obtaining the modified *E. coli* strain comprises deletion of the gene of competing product lactate that is Lactate dehydrogenase (ldhA).

In some embodiments, the method for obtaining the modified *E. coli* strain comprises deletion of gene of competing product acetate that may be selected from Phosphotransacetylase (pta) and Acetate kinase (ack).

In one embodiment, the method for obtaining the modified E. coli strain comprises deletion of gene competing product acetate that is Acetate kinase (ack). The acetate Acetate kinase (ack) gene may be Acetate kinase A(ack A) or Acetate kinase B (ackB).

In one embodiment, the method for obtaining the modified E. coli strain comprises deletion of gene of competing product succinate that can be selected from Fumarate Reductase A (frdA), Fumarate Reductase B (frdB), Fumarate Reductase C (frdC), Fumarate Reductase D (frdD), Succinyl coA synthetase and Isocitrate lyase.

In one embodiment, the method for obtaining the modified E. coli strain comprises deletion of gene of competing product succinate that is Fumarate Reductase A (frdA).

In one embodiment, the method for obtaining the modified E. coli strain comprises deletion of gene of competing product formate that can be selected from Pyruvate formate lyase A (pflA), Pyruvate formate lyase B (pflB), Pyruvate formate lyase C (pflC) and Pyruvate formate lyase D (pflD).

In one embodiment, the method for obtaining the modified E. coli strain comprises deletion of gene of competing product formate that is Pyruvate formate lyase B (pflB).

In some embodiments, the method for obtaining the modified E. coli strain comprises reintroducing the basal level expression of one or more genes of the competing product.

In one embodiment the method for obtaining the modified E. coli strain comprises reintroducing the basal level expression of acetate kinase (ack).

In one embodiment the present invention provides a method of obtaining a modified Escherichia coli strain wherein the method comprises the steps of:
a. replacing the promoter of pyruvate dehydrogenase operon (PDH) with a promoter of a gene that is expressed at high level under anaerobic conditions;
b. introducing mutations by deleting genes responsible for competing products that is lactate, succinate, acetate and formate;
c. reintroducing basal level expression of gene encoding acetate kinase.

In one embodiment the present invention provides a method of obtaining a modified Escherichia coli strain wherein the method comprises the steps of:
a. replacing the promoter of pyruvate dehydrogenase operon (PDH) with a promoter of a gene selected from frdA, ldhA, pflB, adhE and gapA;
b. introducing mutations by deleting genes responsible for competing products that is lactate, succinate, acetate and formate;
c. reintroducing basal level expression of gene encoding acetate kinase.

In preferred embodiment the present invention provides a method of obtaining a modified Escherichia coli strain wherein the method comprises the steps of:
a. replacing the promoter of pyruvate dehydrogenase operon (PDH) with promoter of a gapA gene;
b. introducing mutations by deleting genes responsible for competing products that is lactate, succinate, acetate and formate;
c. reintroducing basal level expression of gene encoding acetate kinase.

In one embodiment the present invention provides a method of fermenting hexose and/or pentose sugars utilizing the modified E. coli strain for the production of bioalcohol.

In one embodiment the present invention provides a method of fermenting hexose sugar wherein the hexose sugar can be selected from glucose, galactose, allose, altrose, mannose, gulose, idose and talose. In one embodiment the present invention provides a method of fermenting hexose sugar wherein the hexose sugar can be glucose and/or galactose. In one embodiment the present invention provides a method of fermenting hexose sugar wherein the hexose sugar is glucose.

In one embodiment the present invention provides a method of fermenting pentose sugar wherein the pentose sugar is selected from xylose, arabinose, ribose, lyxose, ribulose and xylulose. In one embodiment the present invention provides a method of fermenting pentose sugar wherein the pentose sugar can be xylose and/or arabinose. In one embodiment the present invention provides a method of fermenting pentose sugar wherein the pentose sugar is xylose.

In one embodiment the present inventions provides a method of fermenting lignocellulosic biomass comprising hexose and pentose sugars by using the modified bacterial strain.

In some embodiments of the invention, the method of fermenting hexose and pentose sugars comprised in lignocellulosic biomass by using the modified bacterial strain for the production of bioalcohol under aerobic, microaerobic and/or anaerobic conditions.

In one embodiment of the invention, the method of fermenting hexose and pentose sugars comprised in lignocellulosic biomass by using the modified bacterial strain is carried out under microaerobic and/or anaerobic condition.

In one embodiment of the invention, the method of fermenting hexose and pentose sugars comprised in lignocellulosic biomass by using the modified bacterial strain is carried out under microaerobic condition.

In one embodiment the present invention provides method of fermenting lignocellulosic biomass with a modified Escherichia coli strain wherein the method comprises the steps of:
hydrolyzing the lignocellulosic biomass comprising hexose and pentose sugars;
mixing the modified Escherichia coli strain with hydrolyzed lignocellulosic biomass comprising hexose and pentose sugars;
allowing fermentation of the mixture to be carried out in microaerobic conditions to produce ethanol.

In one embodiment, the lignocellulosic biomass is pretreated to obtain a hydrolyzed lignocellulosic biomass.

The present method of obtaining the modified E. coli strain is redox balanced. The modified E. coli strain with promoter of pyruvate dehydrogenase operon (PDH) replaced with promoters of various genes expressed under anaerobic condition showed enhanced ethanol yield particularly when its promoter was replaced with gapA promoter. Deletion of genes of competing products further increased the ethanol yield. Expression of acetate kinase at basal level helped restoring the cell growth rate and improved ethanol productivity significantly. Microaerobic condition further improved the growth rate of the cells on both glucose and xylose. Further, the modified bacterial strain of the present invention process is without introduction of foreign gene, is genetically more stable and capable of fermenting lignocellulosic biomass with enhanced production of ethanol.

The present invention is illustrated by following non-limiting examples.

EXAMPLES

Materials and Methods

Bacterial Strains, Plasmids, Primers, Enzymes and Methods:

List of bacterial strains, plasmids and primers used in the study has been provided in Table 1. *E. coli* DH5α strain (Invitrogen) was used for performing all the cloning work and *E. coli* B (*Coli* Genetic Stock Centre (CGSC), Yale University, USA) was used as parent strain for all the genomic manipulations. Restriction endonuclease and T4 DNA ligase were procured from New England Biolabs. Custom oligonucleotides (primers) were synthesized from Sigma-Aldrich for PCR amplifications. Taq DNA polymerase (Bangalore Genei) was used for performing verification PCR of the engineered strains. Plasmids pKD4, pKD46 and pCP20 (CGSC, USA) were used as the source of FRT-kan-FRT fragment, lambda Red recombinase and flippase, respectively, for performing genetic manipulation. Recombinant DNA techniques were performed according to standard procedures (Sambrook et al., 1989). DNA purification was performed using Qiagen kit. DNA fragments were amplified by Phusion High Fidelity polymerase (Finnzymes) for cloning and template preparation for homologous recombination.

TABLE 1

Strains, plasmids and primers used in the study

| Name | Description | Reference or Source |
|---|---|---|
| Strains | | |
| *E. coli* B F-  | | CGSC #2507 |
| SSY01 | *E. coli* B, ΔPDH-promoter::FRT-kan-FRT-IdhA gene promoter; promoter of pdh gene replaced with promoter of IdhA gene | This study |
| SSY02 | *E. coli* B, ΔPDH-promoter:FRT-kan-FRT-frdA gene promoter | This study |
| SSY03 | *E. coli* B, ΔPDH-promoter:FRT-kan-FRT-pflB gene promoter | This study |
| SSY04 | *E. coli* B, ΔPDH-promoternFRT-kan-FRT-adhE gene promoter | This study |
| SSY05 | *E. coli* B, ΔPDH-promoter:FRT-kan-FRT-gapA gene promoter | This study |
| SSY06 | SSY05 ΔIdhA::FRT-kan-FRT; deletion mutant for IdhA gene in SSY05 host | This study |
| SSY07 | SSY06 ΔfrdA::FRT-kan-FRT; deletion mutant for frdA gene in SSY06 host | This study |
| SSY08 | SSY07 ΔackA::FRT-kan-FRT; deletion mutant for ackA gene in SSY07 host | This study |
| SSY09 | SSY08 ΔpflB::FRT-kan-FRT; deletion mutant for pflB gene in SSY08 host | This study |
| SSY10 | SSY09 transformed with pZSack plasmid | This study |
| SSY11 | SSY09 transformed with pZS*mcs plasmid | This study |
| Plasmids | | |
| pUC19 | bla, cloning vector | |
| pKD4 | bla, FRT-kan-FRT | CGSC #7632 |
| pKD46 | bla, y B exo (red recombinase), temperature-conditional replicon | CGSC #7739 |
| pCP20 | bla, flp, temperature-conditional replicon | CGSC #7629 |
| pSSY01 | FRT-kan-FRT sequence from pKD4 was cloned into pUC19 at EcoRI and BamHI sites | This study |
| pSSY02 | IdhA gene promoter from *E. coli* B was cloned into pSSY01 at BamHI and HindIII sites | This study |
| pSSY03 | frdA gene promoter from *E. coli* B was cloned into pSSY01 at BamHI and HindIII sites | This study |
| pSSY04 | pflB gene promoter from *E. coli* B was cloned into pSSY01 at BamHI and HindIII sites | This study |
| pSSY05 | adhE gene promoter from *E. coli* B was cloned into pSSY01 at BamHI and HindIII sites | This study |
| pSSY06 | gapA gene promoter from *E. coli* B was cloned into pSSY01 at BamHI and HindIII sites | This study |
| pZSblank | $P_{EtetO1}$ expression vector, pSC101*origin, $Cm^R$ | Yazdani et al 2008 |

TABLE 1-continued

Strains, plasmids and primers used in the study

| Name | Description | Reference or Source |
|---|---|---|
| pZS*mcs | multiple cloning site derived from pET28a(+) cloned in pZSblank | This study |
| pZSack | ack gene cloned in pZS*mcs vector | This study |
| Primers | | |
| FRT-kan-FRT-F | GGAGA<u>GAATTC</u>GTGTAGGCTGGAGCTGCTTC | This study |
| FRT-kan-FRT-R | GGAGA<u>GGATCC</u>ATATGAATATCCTCCTTAG | This study |
| IdhA promoter-F | TCG<u>GGATCC</u>GCAAGCTGACAATCTCCC | This study |
| IdhA promoter-R | ACTC<u>AAGCTT</u>AAGACTTTCTCCAGTGATGTTG | This study |
| frdA promoter-F | TGC<u>GGATCC</u>ATCAAACAGCGGTGGGCAG | This study |
| frdA promoter-R | CCC<u>AAGCTT</u>GACATTCCTCCAGATTGTTT | This study |
| pflB promoter-F | TCG<u>GGATCC</u>AACCATGCGAGTTACGGGCCTATAA | S. Zhou et al 2008 |
| pflB promoter-R | CCC<u>AAGCTT</u>GTGCCTGTGCCAGTGGTTGCTGTGA | This study |
| adhE promoter-F | CGC<u>GGATCC</u>CCGGATAATGTTAGCCATAA | This study |
| adhE promoter-R | CCC<u>AAGCTT</u>AATGCTCTCCTGATAATGTTA | This study |
| gapA promoter-F | CGC<u>GGATCC</u>GATTCTAACAAAACATTAACAC | This study |
| gapA promoter-R | CCC<u>AAGCTT</u>ATATTCCACCAGCTATTTGT | This study |
| H1 | *CTCCTTTCCTACGTAAAGTCTACATTTGTGCATAGTTACAACTTTGTGTAGGCTGGA GCTGCTTC* | Zhou et al 2008 |
| H2_IdhA | *GCGAGTTTCGATCGGATCCACGTCATTTGGGAAACGTTCTGACATAAGACTTTCTCC AGTGATGTTG* | This study |
| H2_adhE | *GCGAGTTTCGATCGGATCCACGTCATTTGGGAAACGTTCTGACATAATGCTCTCCTG ATAATGTT* | This study |
| H2_gapA | *GCGAGTTTCGATCGGATCCACGTCATTTGGGAAACGTTCTGACATATATTCCACCAG CTATTTGT* | This study |
| H2_frdA | *GCGAGTTTCGATCGGATCCACGTCATTTGGGAAACGTTCTGACATGACATTCCTCCA GATTGTTC* | This study |
| H2_pflB | *GCGAGTTTCGATCGGATCCACGTCATTTGGGAAACGTTCTGACATGTAACACCTACC TTCTGTTGCTGTGATATAGAAGAC* | Zhou et al 2008 |
| v-PDH-F | TGCATGGTTGAAGATGAGTTG | This study |
| v-PDH-R | TGATGTAGTTGCTGATACCTG | This study |
| pZS-ack-F | GATC<u>GGATCC</u>ATGTCGAGTAAGTTAGTACTGGT | This study |
| pZS-ack-R | TCGA<u>GTCGAC</u>TCAGGCAGTCAGGCGGCTC | This study |

Note:
Homologous region for recombination is in italics and the enzyme sites are underlined Replacing the PDH Operon in the *E. coli* B Genome:

FRT-kan-FRT sequence from pKD4 was amplified using FRT-kan-FRT-F and FRT-kan-FRT-R primers (Table 1), digested with EcoRI and BamHI and ligated to the corresponding restriction endonuclease sites of pUC19 plasmid to generate the plasmid pSSY01. (at the 3' end of FRT-kan-FRT in pSSY01 to produce plasmids pSSY02-06 (Table 1). A 45 bases homologous sequence for −202 to −157 bp upstream of pdhR coding region of PDH operon was added to the 20 bases of 5' end of FRT-kan-FRT sequence to design primer H1 and a 45 bases homologous sequence corresponding to +1 to +45 coding region of aceE of PDH operon was added to 20-22 bases of 3' end of each promoter to obtain primer H2 (Table 1). PCR was performed with the H1 and H2 primers and corresponding plasmid pSSY02-06 as template under following conditions: 98° C. for 2 min, followed by 30 cycles of denaturation at 98° C. for 15 sec, annealing at 59° C. for 15 sec, extension at 72° C. for 2 min and a final extension at 72° C. for 10 min. The PCR product was gel eluted, digested with DpnI, re-purified and electroporated (2.5 KV, 25 µF and 200Ω) into *E. coli* B carrying pKD46 (grown in LB broth with 1 mM L-arabinose at 30° C. till $OD_{600\ nm}$ reaches ~0.3-0.4) to replace the promoter, RBS and pdhR gene of pyruvate dehydrogenase (PDH) operon with the heterologous promoter (Datsenko and Wanner, 2000). Transformants were selected on kanamycin LB-agar plates. The engineered strains (SSY01-05) (Table 1) were verified for the PDH promoter replacement by performing two sets of colony PCR, one set using v-PDH-F (−372 bp upstream of pdhR) and v-PDH-R (+163 bp downstream of start of coding region of aceF) primers to verify native promoter deletion, and second set using forward primer of the heterologous promoter and v-PDH-R to verify introduction of heterologous promoter (data not shown). Before further manipulation, the kanamycin resistance marker gene was removed from the chromosome of the selected strain with the help of FLP recombinase by using the temperature sensitive helper plasmid, pCP20 (Datsenko and Wanner, 2000).

Host gene deletions were achieved through P1 transduction method (Miller, 1972) using the single gene knockout Keio strains from CGSC, Yale University, USA (Baba et al., 2006). The kanamycin resistant marker gene was removed as described above and the resultant strain was used for sequential rounds of gene knockout.

Construction of pZSack Plasmid:

MCS of pET28a(+) (Novagen) was amplified and cloned in pZSblank plasmid (Yazdani and Gonzalez, 2008) to obtain pZS*mcs. The ackA gene encoding acetate kinase was amplified from E. coli B genome using pZS-ack-F and pZS-ack-R primers, digested with BamHI and SalI and the resultant fragment was ligated into the BamHI-SalI sites of pZS*mcs to produce pZSack. The pZSack plasmid was then electroporated into SSY09 for enhancement of growth rate.

Media and Culture Conditions:

Bacterial strains were grown in either LB medium or Morpholino-propanesulfonic (MOPS) defined medium. Antibiotics were added as appropriate with ampicillin at 50 µg/ml, kanamycin at 30 µg/ml and chloramphenicol at 34 µg/ml. For checking production of metabolites by the engineered strains in the tube, the strains were grown overnight at 37° C. on LB agar plates containing relevant antibiotic and an isolated colony was inoculated in Hungate tube filled until brim (17.5 ml) with 1× MOPS or LB medium supplemented with antibiotics and desired sugar (glucose, xylose, galactose or arabinose) as carbon source. In the study where engineered strains were transformed with pZSack or pZS*mcs plasmid, the cells were grown in the Hungate tube filled with media containing 0, 0.1 or 100 ng/ml of anhydrotetracycline as inducer and 34 µg/ml of chloramphenicol as antibiotic. The tubes were incubated at 37° C. under rotating condition and harvested at different intervals. The optical density of the grown culture was recorded at 600 nm and supernatant was saved for metabolite analysis via HPLC.

The engineered strains were cultivated in the bioreactor to evaluate their performance under controlled environment at various stages of manipulation. Primary culture was prepared by incubating an isolated colony from agar plate into 17.5 ml MOPS medium containing 2.5 g/l glucose in Hungate tube for 24 hr at 37° C. In case of the engineered cells where ack and pflB genes were deleted (i.e., SSY09 and SSY10), primary culture was adapted to anaerobic condition in 100 ml LB medium in a 250 ml flask containing 2.5 g/l glucose or xylose for 48 hr at 37° C. in anaerobic chamber (Bactron II, Shel lab). Appropriate volume of the culture to achieve initial $OD_{600\ nm}$ of 0.05 in the bioreactor was centrifuged at 4000 rpm for 4 min and re-suspended in fresh medium. The culture was inoculated in one of the six 0.5 L vessels of Biostat Q plus fermentor (Sartorius) containing 350 ml of MOPS or LB medium having appropriate amount of sugar. The vessels were controlled independently at 37° C., 300 rpm and pH 6.8. High purity Argon gas was purged in the medium to create anaerobic environment at a rate of 0.02 L/min. In case of fermentation under microaerobic condition, compressed air was passed in the headspace of the vessel at the rate of 0.02 L/min at which dissolved oxygen probe demonstrated zero reading throughout the fermentation. Samples collected from fermentor vessels at various time intervals were used to calculate cell growth, substrate utilization and product synthesis.

Enzyme Assay:

To check the activity of PDH enzyme under anaerobic conditions, engineered E. coli B strains with heterologous PDH promoter along with wild type strain as control were grown in Hungate tubes filled with LB medium+2% glucose for 12 hr at 37° C. Cells were harvested by centrifugation (5 min, 5000 rpm), washed twice with 9 g/l NaCl and stored as cell pellets at −20° C. Cell pellets were resuspended in 0.1 M potassium phosphate buffer (pH 8.0) to obtain $OD_{600}$ of 10 and were permeabilized with chloroform. The reaction was set-up in 1 ml in the cuvette containing 50 mM potassium phosphate buffer (pH 8.0), 2.0 mM sodium pyruvate, 2.5 mM $NAD^+$, 0.2 mM thiamine pyrophosphate, 1.0 mM $MgCl_2$, 0.13 mM CoA, 2.6 mM cysteine hydrochloride. Permeabilized cells (25 µl) were added to start the reaction and the pyruvate dehydrogenase activity was measured by detecting change in absorbance at 340 nm (Ultrospec 3100 pro, Amersham Biosciences) (Danson et al., 1978). Substrate blank where no sodium pyruvate was added served as control. Enzyme activity was calculated as nmol NADH formed/min/mg of cell protein. A protein content of 50% (wt/wt) with respect to dry cell mass was assumed in these calculations. Significance of differences between enzyme activities of test and control cells was determined using one-tailed unpaired Student's t-test. P value of 0.05 and less was considered statistically significant.

Analytical Methods:

Extracellular metabolites of the grown culture were determined as follows. Culture of the grown cells was centrifuged at 13200 rpm for 5 min. The aqueous supernatant was filtered and used for HPLC analysis. The metabolite separation was achieved using the HPLC system (Agilent technologies) attached with Aminex HPX-87 H anion exchange column (Bio-Rad). The filtered and degassed mobile phase (4 mM $H_2SO_4$) was used at a constant rate of 0.3 ml/min with column and RI detector temperatures maintained at 40° C. and 35° C., respectively. Standards of the metabolites (Absolute Standards, USA) at 1 g/l were separated on HPLC column and areas obtained were used to calculate metabolite concentration in the text samples. Cell density was measured at an optical density 600 nm ($OD_{600}$) in a spectrophotometer (RioRad). Dry cell mass was calculated by drying cell pellets of defined $OD_{600}$ at 75° C. in oven for 20 hr. The $OD_{600}$ of 1.0 corresponded to 0.56 mg dry mass per ml of culture. The values obtained for cell biomass, substrate utilization and product synthesis were used for calculation of biomass and product yields (mmol/mmol substrate), specific productivity (mmol/gcell/h) and volumetric productivity (mmol/L/h). For calculating biomass yield we used a molecular formula of cells as $CH_{1.9}O_{0.5}N_{0.2}$ with an average molecular weight of 24.7.

Supplementary Methods:

Quantitative Real-Time RCR:

E. coli B and SSY05 strains were grown as described above. Total RNA was isolated and 2 µg RNA from each was reverse-transcribed using Superscript RT III (Invitrogen). 2 µl of this reaction mix was added in a final volume of 20 µl and amplified using the QuantiMix Easy HRM kit (Biotools) with gene specific primers. After an initial activation at 50° C. for 2 min and a preincubation step at 95° C. for 10 min, reaction mixtures were subjected to 40 cycles of denaturation at 95° C. for 15 sec, annealing at 56° C. for 30 sec and extension at 72° C. for 35 sec (Bio-Rad iCycler). This was followed by a dissociation curve analysis at 95° C. for 15 sec, 60° C. for 20 sec and 95° C. for 15 sec. Data analysis was done as described by Pfaffl method (Pfaffl, 2001). and dnaA gene was taken as the internal control. Reaction mixtures without the reverse transcriptase and without the RNA template were taken as the negative controls for the experiment. All experiments were done in triplicate.

promoter of PDH operon with the promoter of the gene known to express under anaerobic condition. In the absence of information in the literature regarding relative strength of promoters of the genes expressed under anaerobic condition, promoters of five genes, frdA, ldhA, pflB, adhE and gapA, were selected and native promoter of PDH operon is replaced. The resultant transformants were verified by internal template based and external host chromosomes based primers and were designated as SSY01 to SSY05 for

TABLE 2

Fermentation parameters for cell growth, sugar utilization and Product synthesis at the bioreactor level

| Sugar | Strain | Medium + Sugar Conc.$^a$ | Product Yield (mmol per mmol sugar) | | | | | | % Theoretical yield of ethanol$^b$ | Max ethanol productivity$^c$ | |
|---|---|---|---|---|---|---|---|---|---|---|---|
| | | | Cells | Succinate | Lactate | Formate | Acetate | Ethanol | | Specific (mmol/g/h) | Volumetric (mmol/l/h) |
| Glucose | E. coli B | Defined medium + 20 g/l | 0.36 | 0.11 | 0.42 | 1.19 | 0.51 | 0.65 | 32 | 4.82 | 4.72 |
| | SSY05 | Defined medium + 20 g/l | 0.40 | 0.14 | 0.13 | 0.98 | 0.42 | 0.84 | 42 | 5.76 | 6.19 |
| | SSY06 | Defined medium + 20 g/l | 0.42 | 0.14 | 0.02 | 1.15 | 0.53 | 0.96 | 48 | 6.42 | 6.91 |
| | SSY07 | Defined medium + 20 g/l | 0.46 | 0.01 | 0.03 | 1.16 | 0.46 | 1.08 | 54 | 4.85 | 5.97 |
| | SSY10 | Defined medium + 20 g/l | 0.25 | 0.00 | 0.00 | 0.00 | 0.12 | 1.67 | 83 | 4.00 | 1.62 |
| | E. coli B | LB medium + 50 g/l | 0.23 | 0.07 | 0.78 | 0.57 | 0.37 | 0.31 | 16 | 6.15 | 3.06 |
| | SSY10 | LB medium + 50 g/l | 0.16 | 0.01 | 0.01 | 0.03 | 0.07 | 1.89 | 95 | 20.03 | 12.34 |
| Xylose | E. coli B | Defined medium + 20 g/l | 0.34 | 0.17 | 0.00 | 1.21 | 0.80 | 0.61 | 36 | 2.46 | 1.54 |
| | SSY10 | Defined medium + 20 g/l | 0.24 | 0.01 | 0.02 | 0.00 | 0.14 | 1.09 | 68 | 6.15 | 1.96 |
| | E. coli B | LB medium + 50 g/l | 0.20 | 0.10 | 0.05 | 0.30 | 0.70 | 0.79 | 47 | 3.13 | 1.90 |
| | SSY10 | LB medium + 50 g/l | 0.18 | 0.02 | 0.01 | 0.03 | 0.26 | 0.91 | 55 | 1.57 | 1.67 |
| | SSY10 | LB medium + 50 g/l (Microaerobic, pH 6.3) | 0.40 | 0.01 | 0.01 | 0.01 | 0.17 | 1.63 | 97 | 5.72 | 6.84 |
| Glucose + Xylose | SSY10 | LB medium + 50 g/l (Microaerobic, pH 6.3) | 0.64 | 0.01 | 0.00 | 0.00 | 0.04 | 1.61 | 85 | 5.43 | 14.94 |

$^a$Growth condition in the fermenter is described herein above.
$^b$% Theoretical yield of ethanol was calculated by considering theoretical maximum yield of 2 mmol of ethanol per mmol of glucose and 1.67 mmol of ethanol per mmol of xylose as 100%.
$^c$Maximum specific (mmol ethanol per gram of cells per hour) and volumetric (mmol per liter of culture per hour) productivity of ethanol were calculated by accounting the interval at which maximum substrates were consumed and maximum products and cell biomass were formed.

Promoter Replacement of Pyruvate Dehydrogenase (PDH) Operon Enhances its Activity and Ethanol Yield Under Anaerobic Condition Ethanol production in E. coli through pyruvate formate lyase (PFL) pathway is short of reducing equivalent to achieve a theoretical maximum yield via fermentation of pentose and hexose sugars (FIG. 1). FIG. 1 shows the metabolic pathways of E. coli functional under anaerobic conditions during glucose and xylose fermentation. Relevant genes and corresponding enzymes are shown. Pyruvate dehydrogenase (PDH) operon was expressed under anaerobic condition via promoter replacement and is represented as thick line. The competing pathways to ethanol were blocked as shown by two parallel bars. Broken arrows represent multiple reactions of a pathway. Extracellular metabolites are placed in boxes. Abbreviations are as follows: ADH, acetaldehyde/alcohol dehydrogenase; ACK, acetate kinase; FHL, formate hydrogen-lyase; FRD, fumarate reductase; LDH, actate dehydrogenase; PDH, pyruvate dehydrogenase; PFL, pyruvate formate-lyase; PTA, phosphate acetyltransferase; PYK, pyruvate kinase. Therefore, wild type E. coli typically produces mixed acids under fermentative condition with only fraction of carbon goes towards ethanol. The redox balance for homoethanol production may be achieved upon optimal activation of pyruvate dehydrogenase (PDH) pathway under anaerobic condition (FIG. 1). The operon encoding PDH complex is usually repressed under anaerobic condition through global repressor binding to its promoter. To prevent this repression, it was decided to replace the promoter of PDH operon with the promoter of the gene known to express under anaerobic condition. In the absence of information in the literature regarding relative strength of promoters of the genes expressed under anaerobic condition, promoters of five genes, frdA, ldhA, pflB, adhE and gapA, were selected and native promoter of PDH operon is replaced. The resultant transformants were verified by internal template based and external host chromosomes based primers and were designated as SSY01 to SSY05 for $P_{ldhA}$PDH, $P_{frdA}$PDH, $P_{adhE}$PDH, $P_{pflB}$PDH and $P_{gapA}$PDH promoters, respectively (Table 1).

Figure 2:
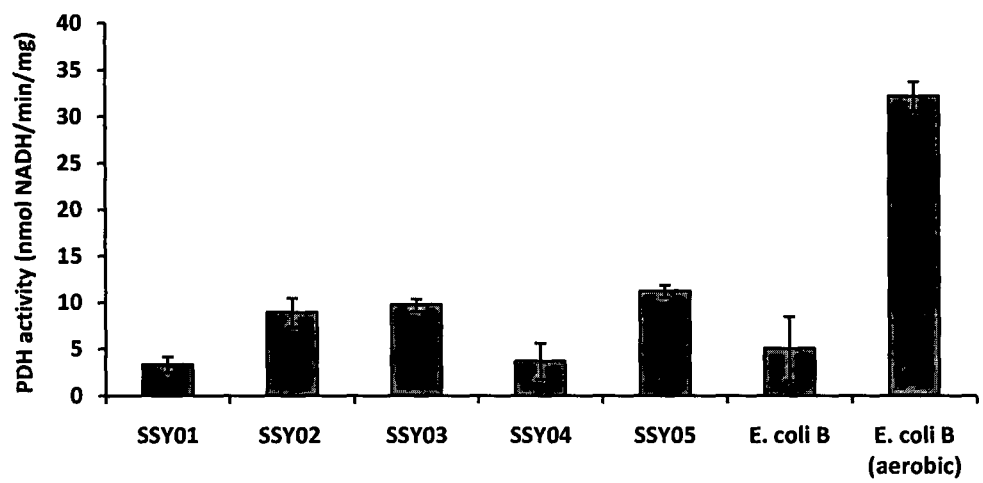
FIG. 2A is a graph showing the functional characterization of promoter engineered E. coli B strains (SSY01-05) and the effect of PDH operon promoter replacement on pyruvate dehydrogenase activity
FIG. 2B is a graph showing the functional characterization of promoter engineered E. coli B strains (SSY01-05) and the effect of PDH operon promoter replacement on ethanol production
Figure 2:

The engineered cells were grown under anaerobic condition and used for measuring pyruvate dehydrogenase (PDH) activity. The results indicated 0.6-2.2 fold change in PDH activity between various promoter-engineered strains (FIG. 2A). FIG. 2A is a graph showing the functional characterization of promoter engineered E. coli B strains (SSY01-05, Table 1) and shows the effect of PDH operon promoter replacement on pyruvate dehydrogenase activity. Cells were grown anaerobically in completely filled Hungate tubes and were harvested and permeabilized to measure PDH activity. E. coli B grown under aerobic condition was used as positive control. The supernatant of the culture was used to analyze metabolite concentration via HPLC. Percentage improvement in ethanol yield was calculated by comparing ethanol yield (mol of ethanol per mol of sugar) of each strain with respect to E. coli B.

Figure 10:
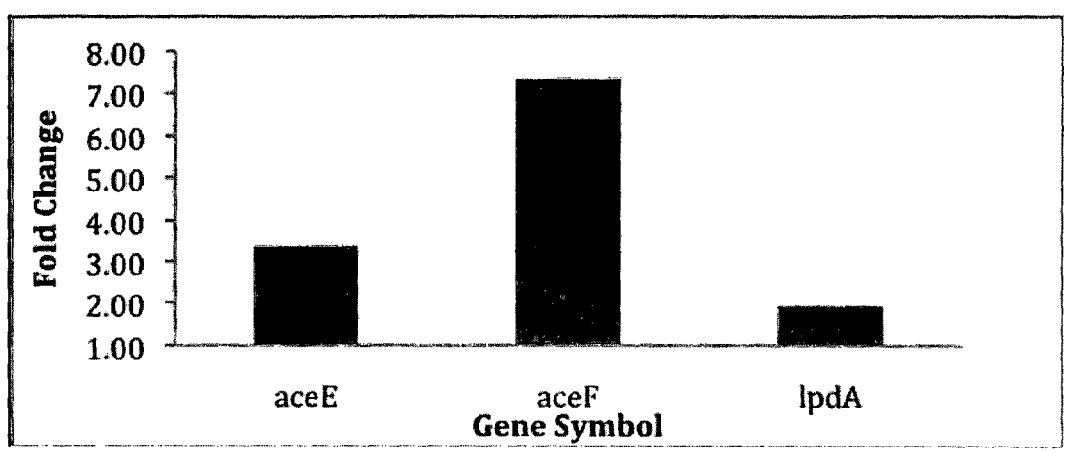
FIG. 10 is a graph showing the validation of expression of PDH operon in promoter replaced SSY05 strain by quantitative real-time PCR.

PDH activities in SSY03 (P=0.045) and SSY05 (P=0.033) strains were significantly higher than the wild type. Transcript levels of aceE, aceF and lpd genes of PDH operon also showed 2-7 fold higher expression in SSY05 strain as compared to wild type (Supplementary FIG. 10). FIG. 10 is a graph showing the validation of expression of PDH operon in promoter replaced SSY05 strain by quantitative real-time PCR. E. coli B and SSY05 strain was grown anaerobically in Hungate tubes filled with LB+2% glucose for 12 hr and RNA was isolated for performing Real Time PCR with gene specific primers corresponding to aceE, aceF and lpdA of PDH operon. Values of each gene were normalized to dnaA gene and are plotted with respect to the control, E. coli B, that has arbitrarily been taken as 1.

Higher PDH activity of promoter-engineered strains under anaerobic condition may account for higher NADH availability and greater carbon flux towards ethanol. Concentration of metabolic products of SSY01 to SSY05 strains was measured after growing them in Hungate tubes filled with defined media containing one of the four sugars commonly present in lignocellulosic biomass, i.e., glucose, xylose, arabinose or galactose. All the promoter-engineered strains, except SSY01 ($P_{ldhA}$PDH), showed improvement in ethanol yield when hexose sugars glucose and galactose were used as carbon source (FIG. 2B, Table 1). FIG. 2B is a graph showing the functional characterization of promoter engineered E. coli B strains (SSY01-05, Table 1) and shows the effect of PDH operon promoter replacement on ethanol production. Cells were grown anaerobically in completely filled hungate tubes and were harvested and permeabilized to measure PDH activity. E. coli B grown under aerobic condition was used as positive control. The supernatant of the culture was used to analyze metabolite concentration via HPLC. Percentage improvement in ethanol yield was calculated by comparing ethanol yield (mol of ethanol per mol of sugar) of each strain with respect to E. coli B. The results were, however, variable in the case of pentose sugars xylose and arabinose. Nevertheless, SSY05 strain showed highest increase in ethanol yield against all the four sugars and therefore was considered for further study.

Figure 3:
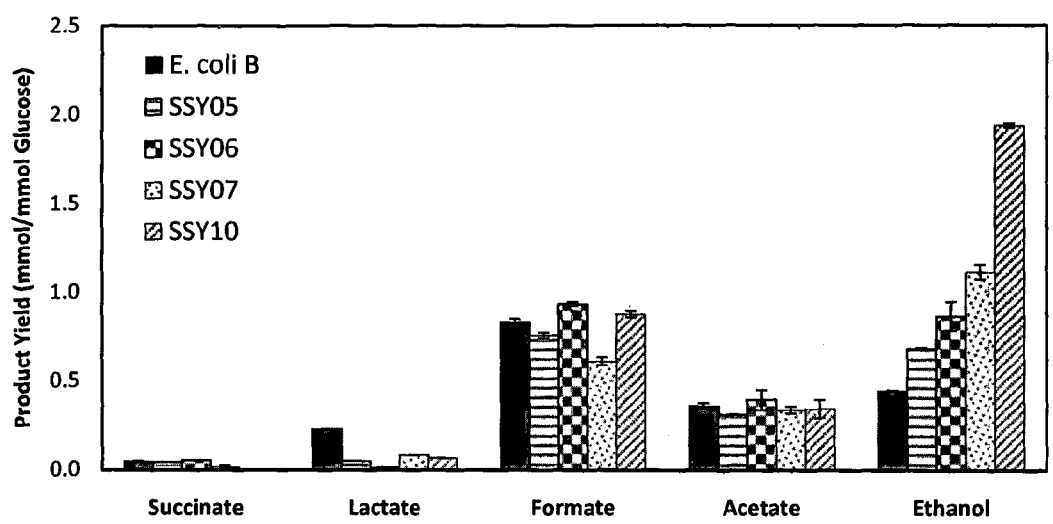
FIG. 3 is a graph showing comparison of product yields of deletion mutants of SSY05.
Figure 4:
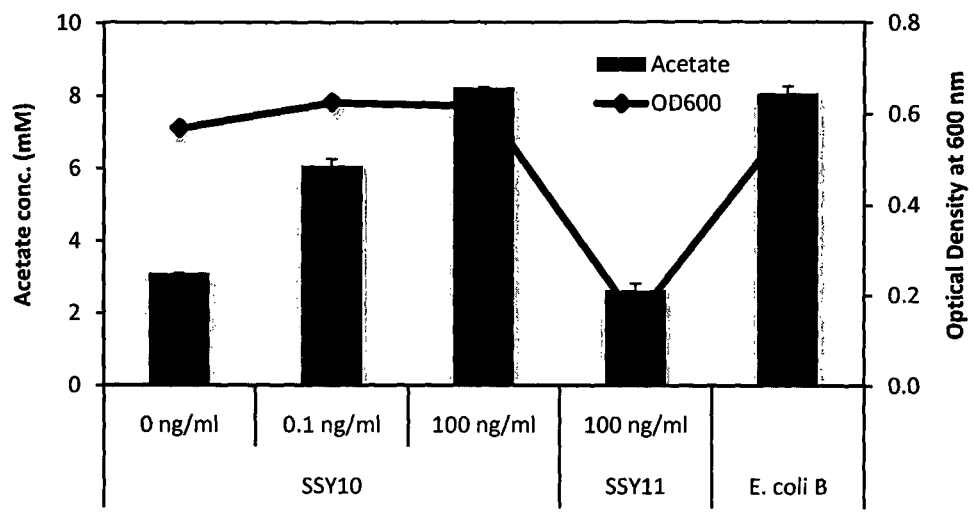
FIG. 4A is a graph showing improvement in cell growth upon basal level expression of ack gene in the engineered SSY09 strain. SSY09 strain was transformed with pZSack was grown in LB media+2.5 g/l glucose
FIG. 4B is a graph showing improvement in cell growth upon basal level expression of ack gene in the engineered SSY09 strain. SSY09 strain was transformed with pZSack was grown in LB media+2.5 g/l xylose
Figure 4:
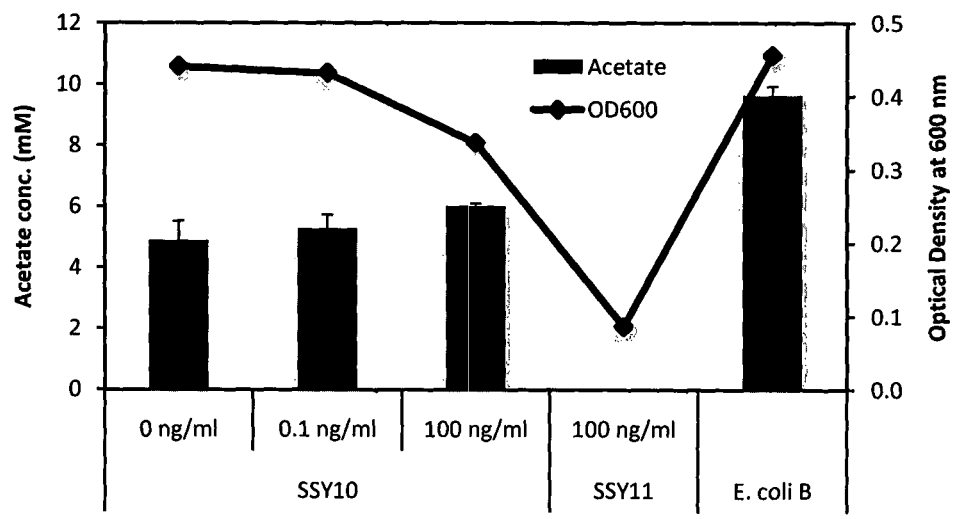

Deletion of Competing Pathways Improves Ethanol Yield in the Engineered SSY05 Strain:

Though the PDH promoter engineered SSY05 strain exhibited significant enhancement in the ethanol level as compared to the wilde type strain, it still produced considerable amount of competing co-products such as lactate, succinate, acetate and formate (Table 1). To further improve ethanol yield, deletion in the genes was introduced for lactate dehydrogenase (ldhA), fumarate reductase (frdA), acetate kinase (ack) and pyruvate formate lyase (pflB) responsible for the formation of lactate, succinate, acetate and formate, respectively, to obtain SSY06 ($P_{gapA}$ PDH ΔldhA), SSY07 ($P_{gapA}$ PDH ΔldhA ΔfrdA), SSY08 ($P_{gapA}$ PDH ΔldhA ΔfrdA Δack) and SSY09 ($P_{gapA}$ PDH ΔldhA ΔfrdA Δack ΔpflB) strains (Table 1). When grown in the Hungate tube containing defined medium under anaerobic condition, SSY06 and SSY07 grew normally and produced ethanol with the yield of 0.87 and 1.11 mmol per mmol glucose, respectively (FIG. 3). FIG. 3 is a graph showing comparison of product yields of deletion mutants of SSY05. Cells were grown in Hungate tube filled with LB medium and 2.5 g/L glucose at 37° C. for 24 hr were harvested and supernatant was used for detection and analysis of product yield. Data represents average and standard deviation from three independent experiments and indicates successive improvement in ethanol yield upon deletions of competing pathways. However, SSY08 grew very slowly and SSY09 did not grow at all. This observation indicated that deletion of ack had deleterious impact on cell growth, possibly due to corresponding depletion of ATP pool. To regain the cell growth, ack gene is introduced through a very low copy plasmid in SSY09 strain to obtain SSY10 strain Significant improvement is found in cell growth upon transformation with the plasmid containing ack gene (SSY10) as compared to the strain transformed with the control plasmid (SSY11) even without addition of the inducer, indicating minor leaky expression of ack gene (FIGS. 4A and 4B). FIG. 4 is a graph showing improvement in cell growth upon basal level expression of ack gene in the engineered SSY09 strain. SSY09 strain was transformed with pZSack was grown in Hungate tube completely filled with LB media+2.5 g/l glucose (A) or 2.5 g/l xylose (B) at 37° C. for 36 hr. Acetate kinase expression was induced with 0, 0.1, 100 ng/ml of anhydrotetracycline. E. coli B and SSY09 transformed with pZS*mcs plasmid were used as positive and negative control, respectively. Results indicate improvement in growth of PZSack transformed cells as compared to control plasmid and less acetate production as compared to wild type strain. Acetate level in uninduced SSY10 strain was less than 50% of the wild type strain and this strain demonstrated ethanol yield of 1.9 mmol per mmol glucose (FIG. 3). ethanol-producing capability of all the engineered strains is further tested at the bioreactor level under controlled environmental condition.

Figure 5:
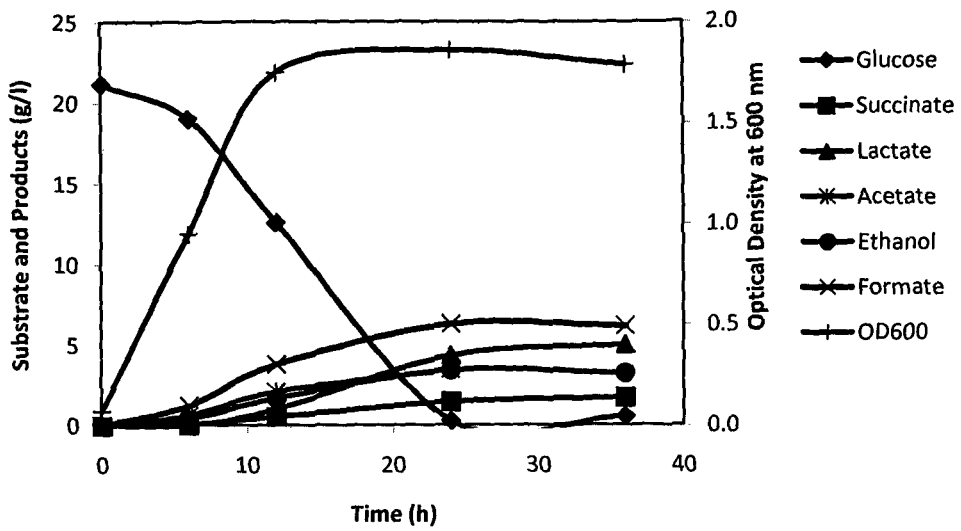
FIG. 5A is a graph showing the fermentation profile of E. coli B grown in the bioreactor in defined medium with glucose as carbon source.
FIG. 5B is a graph showing the fermentation profile of E. coli B grown in the bioreactor in defined medium with xylose as carbon source.
Figure 5:
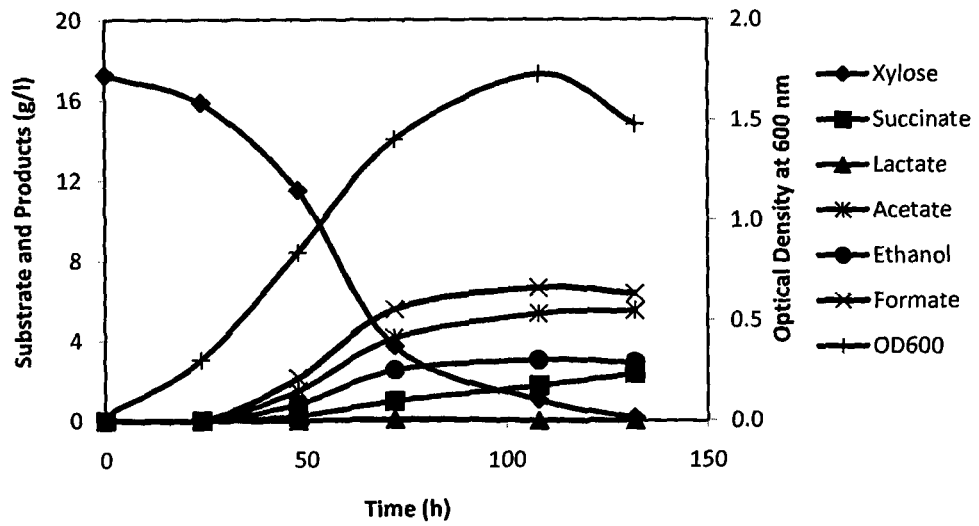
Figure 6:
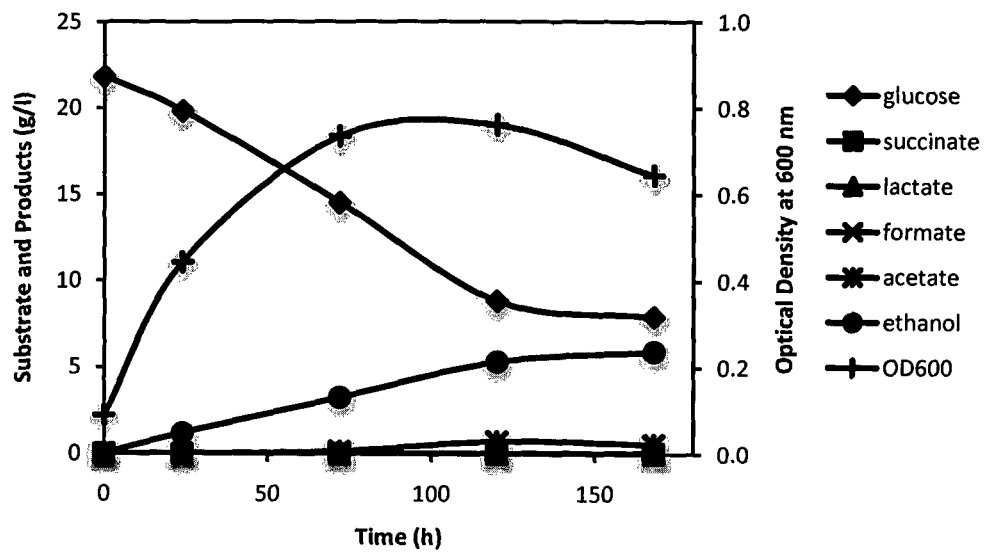
FIG. 6A is a graph showing fermentation profile of SSY10 (SSY09+pZSack) grown in the bioreactor in defined medium with glucose as carbon source. Strain description: SSY10-$P_{gapA}$PDH ΔldhA ΔfrdA Δack ΔpflB (pZSack).
FIG. 6B is a graph showing fermentation profile of SSY10 (SSY09+pZSack) grown in the bioreactor in defined medium with xylose as carbon source. Strain description: SSY10-$P_{gapA}$PDH ΔldhA ΔfrdA Δack ΔpflB (pZSack).
Figure 6:
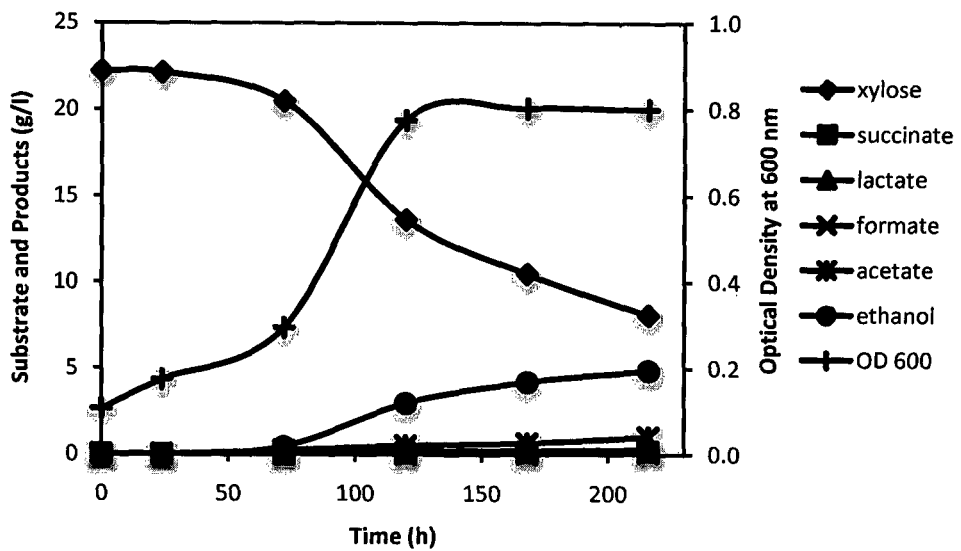

Comparison of Engineered Strains for Ethanol Production at the Bioreactor Level in Defined Medium:

When grown in a bioreactor, wild type E. coli B produced ethanol at the yield of 0.65 and 0.61 mmol per mmol of glucose and xylose, respectively, in defined medium under anaerobic condition as against the theoretical maximum yield of 2 and 1.67 mmol per mmol of these sugars due to generation of competing co-products (FIGS. 5A and 5B, Table 2). FIG. 5 is a graph showing the fermentation profile of E. coli B grown in the bioreactor in defined medium with glucose (A) and xylose (B) as carbon source. Competing products of ethanol are produced at significant level during fermentation of both glucose and xylose in E. coli B. The promoter engineered SSY05 strain showed 10% higher ethanol yield as compared to wild type strain, indicating favourable redox balance towards ethanol production (Table 2). As in the case of Hugate tube data, successive deletion made in the competing pathways to generate SSY06, SSY07 and SSY10 strains resulted in corresponding increase in ethanol and decrease in co-product yield (Table 2). SSY10 strain grown in defined medium with 20 g/l glucose or xylose at the bioreactor level produced ethanol at 83% or 68% of theoretical maximum yield, respectively (FIGS. 6A and 6B, Table 2). FIG. 6 is a graph showing fermentation profile of SSY10 (SSY09+pZSack) grown in the bioreactor in defined medium with glucose (A) and xylose (B) as carbon source. SSY10 primarily produced ethanol. Strain description: SSY10-$P_{gapA}$PDH ΔldhA ΔfrdA Δack ΔpflB (pZSack). However, ~25% of substrate remained unutilized at ~200 hrs of fermentation and ethanol was produced at the low volumetric productivity of 1.6-1.9 mmol/l/h.

Figure 7:
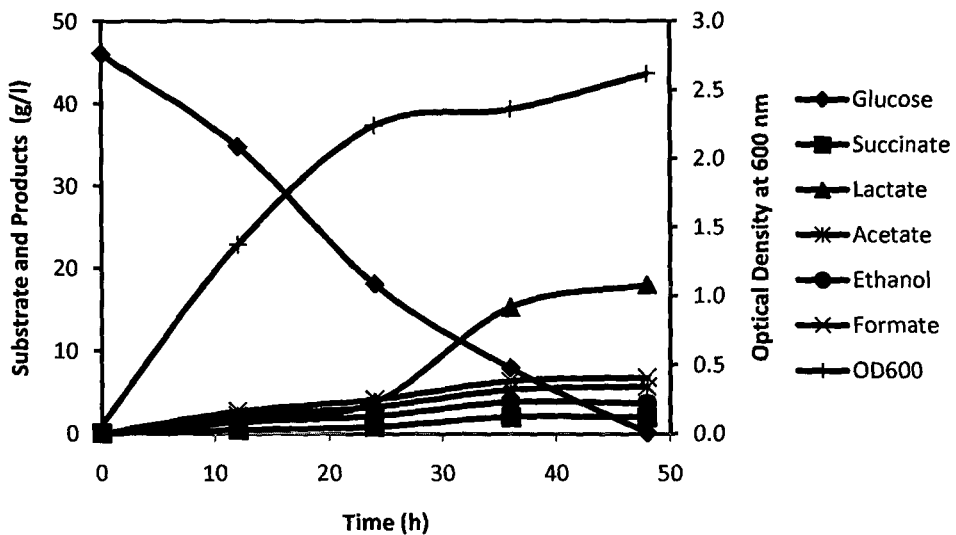
FIG. 7A is a graph showing the fermentation profile of E. coli B grown in the bioreactor in complex medium with glucose as carbon source.
FIG. 7B is a graph showing the fermentation profile of E. coli B grown in the bioreactor in complex medium with xylose as carbon source.
Figure 7:
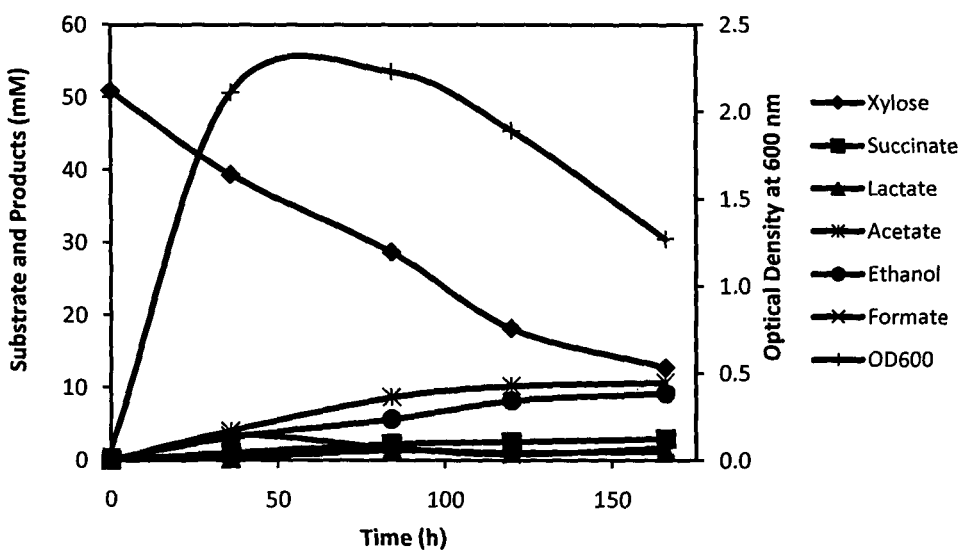
Figure 8:
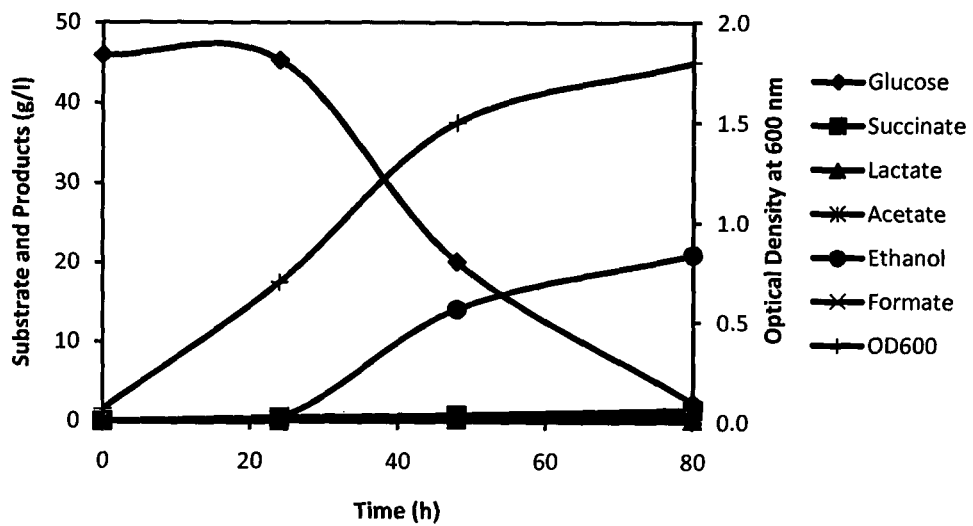
FIG. 8A is a graph showing the fermentation profile of SSY10 (SSY09+pZSack) grown in the bioreactor in complex medium with glucose as carbon source. Strain description: SSY10-$P_{gapA}$PDH ΔldhA ΔfrdA Δack ΔpflB (pZSack).
FIG. 8B is a graph showing the fermentation profile of SSY10 (SSY09+pZSack) grown in the bioreactor in complex medium with xylose as carbon source. Strain description: SSY10-$P_{gapA}$PDH ΔldhA ΔfrdA Δack ΔpflB (pZSack).
Figure 8:
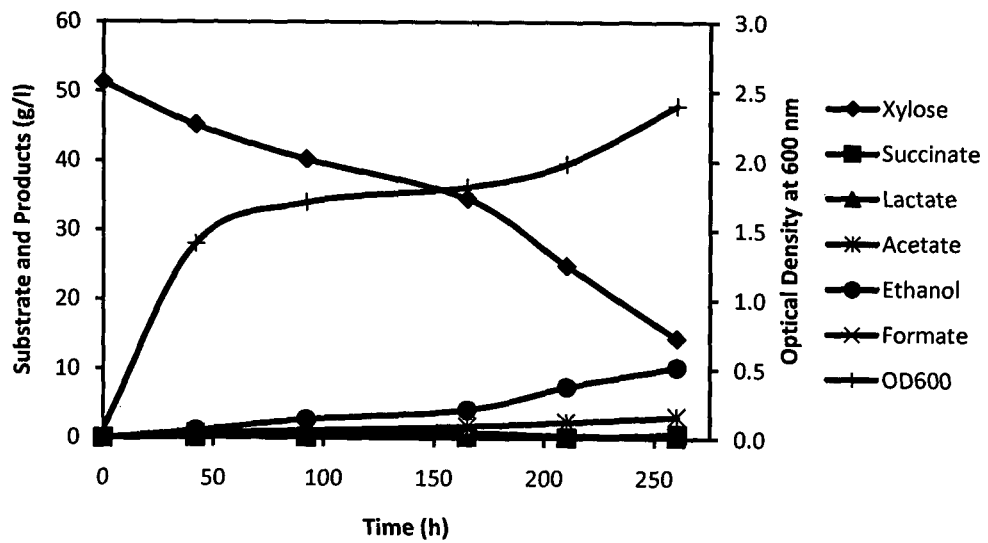

Comparison of Engineered Strains for Ethanol Production at the Bioreactor Level in Complex Medium:

To improve the growth, substrate utilization and ethanol production rate, the engineered cells are grown in LB medium with 50 g/l substrate. The wild type strain produced lactate and acetate as major metabolic products with ethanol produced at the yield of 0.31 and 0.79 mmol per mmol glucose and xylose, respectively (FIGS. 7A and 7B, Table 2). FIG. 7 is a graph showing the fermentation profile of E. coli B grown in the bioreactor in complex medium with glucose (A) and xylose (B) as carbon source. Only small fraction of carbon has been used by the E. coli B cells to produce ethanol. Remarkable improvement in growth rate was observed in the case of SSY10 strain, which produced ethanol at the rate of 12.34 mmol/l/h with 95% of the theoretical yield when glucose was used as carbon source (Table 2). The final ethanol concentration achieved was 21 g/l (457 mM) from 44 g/l (242 mM) glucose in 80 h (FIG. 8A). FIG. 8A is a graph showing the fermentation profile of SSY10 (SSY09+pZSack) grown in the bioreactor in complex medium with glucose as carbon source. SSY10 strain utilized glucose and produced ethanol at a significantly high rate. Strain description: SSY10-$P_{gapA}$PDH ΔldhA ΔfrdA Δack ΔpflB (pZSack).

Figure 9:
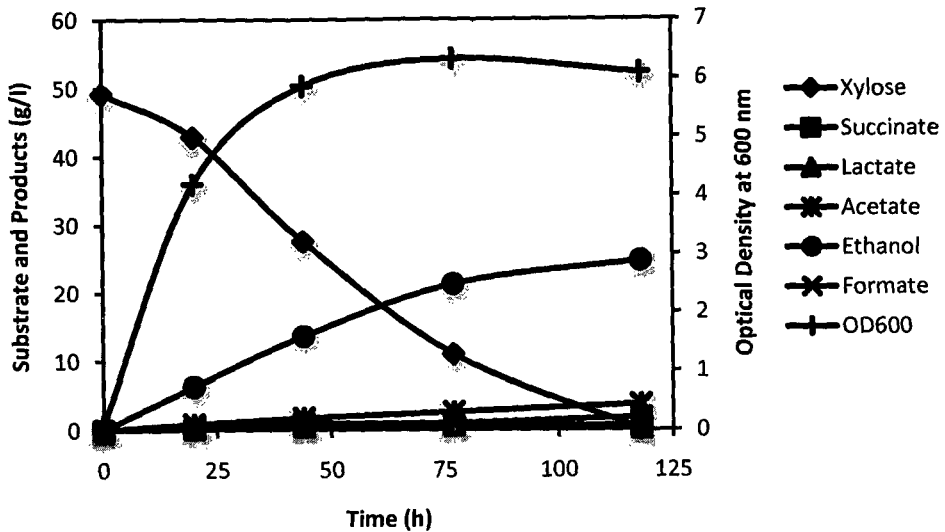
FIG. 9A is a graph showing the fermentation profile of SSY10 (SSY09+pZSack) strain grown under microaerobic condition in the bioreactor in complex medium with xylose as carbon source. Strain description: SSY10-$P_{gapA}$PDH ΔldhA ΔfrdA Δack ΔpflB (pZSack).
FIG. 9B is a graph showing the fermentation profile of SSY10 (SSY09+pZSack) strain grown under microaerobic condition in the bioreactor in complex medium with mixture of glucose and xylose as carbon source. Strain description: SSY10-$P_{gapA}$PDH ΔldhA ΔfrdA Δack ΔpflB (pZSack).
Figure 9:
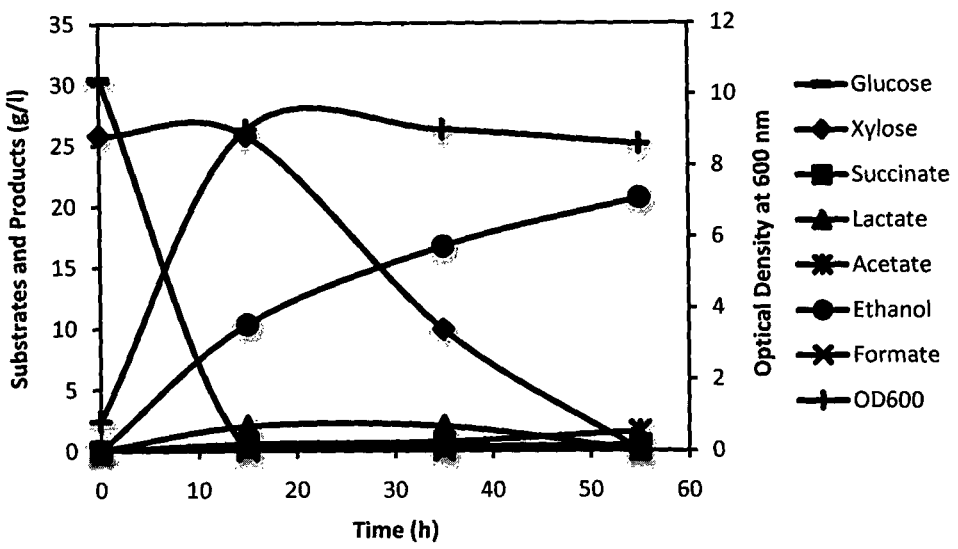

The xylose utilization rate, however, was still slow in the SSY10 strain with 25% xylose remained unutilized after 260 h of fermentation and ethanol produced only at the rate of 1.67 mmol/l/h (FIG. 8B, Table 2). FIG. 8B is a graph showing the fermentation profile of SSY10 (SSY09+pZSack) grown in the bioreactor in complex medium with xylose as carbon source. Xylose utilization rate of SSY10 strain however, was still slow. Strain description: SSY10-$P_{gapA}$PDH ΔldhA ΔfrdA Δack ΔpflB (pZSack). There was a slight increase in xylose utilization rate when pH of the cultivation was maintained at 6.3 (data not shown), possibly due to higher activity of a xylose/proton symporter. To enhance the growth rate of the cells, a microaerobic condition was introduced by passing compressed air in the headspace of bioreactor at a very slow flow rate. Cell growth and xylose utilization rate improved significantly with 50 g/l xylose utilized in 115 h and 25 g/l ethanol produced at the rate of 6.84 mmol/l/h with 97% of the maximum theoretical yield (FIG. 9A). FIG. 9A is a graph showing the fermentation profile of SSY10 (SSY09+pZSack) strain grown under microaerobic condition in the bioreactor in complex medium with xylose as carbon source. The profile indicated efficient utilization of xylose under microaerobic conditions and production of ethanol with high yield and productivity. Strain description: SSY10-$P_{gapA}$PDH ΔldhA ΔfrdA Δack ΔpflB (pZSack). This yield of ethanol from xylose was higher than those reported in the literature from the engineered E. coli without the foreign genes. Utilization of mixture of glucose and xylose is further tested at 25 g/l each under micro-aerobic condition and it is found that there is complete utilization of sugars in 55 hrs with ethanol produced at the rate of 14.94 mmol/l/h (~0.7 g/l/h) with 85% of the maximum theoretical yield (FIG. 9B). FIG. 9B is a graph showing the fermentation profile of SSY10 (SSY09+pZSack) strain grown under microaerobic condition in the bioreactor in complex medium with mixture of glucose and xylose as carbon source. The profile indicated efficient utilization of mixture of glucose and xylose under microaerobic condition and production of ethanol with high yield and productivity. Strain description: SSY10-$P_{gapA}$PDH ΔldhA ΔfrdA Δack ΔpflB (pZSack). This rate of ethanol production was close to the co-fermenting recombinant E. coli KO11 strain at 0.8-0.9 g/l/h. None of the reports published before for the engineered E. coli without the foreign genes demonstrated co-utilization of glucose and xylose.

The engineered E. coli SSY10 strain certainly has advantage over the other engineered E. coli strains such as KO11 for not having any foreign genes responsible for ethanol production. E. coli KO11 has been found to lose its ethanologenicity progressively when cultivated on hemicellulosic sugars in the chemostat culture, possibly due to the genetic instability. Since E. coli SSY10 did not have any foreign genes, its ethanologenic property is expected to be stable for much longer generation and therefore this strain was considered for further studies to evaluate ethanol production from lignocellulosic hydrolysates.

The present invention shows that promoter of pyruvate dehydrogenase operon (PDH) in E. coli was replaced with promoters of various genes expressed under anaerobic condition and that PDH expression and ethanol yield was maximum under anaerobic condition when its promoter was replaced with gapA promoter. Deletion of pathways for competing products further increased the ethanol yield. However, there was significant drop in cell growth rate. Expression of acetate kinase at basal level helped restoring the cell growth rate and improved ethanol productivity significantly. Microaerobic condition further improved the growth rate of the cells on both glucose and xylose.

Figure 11:
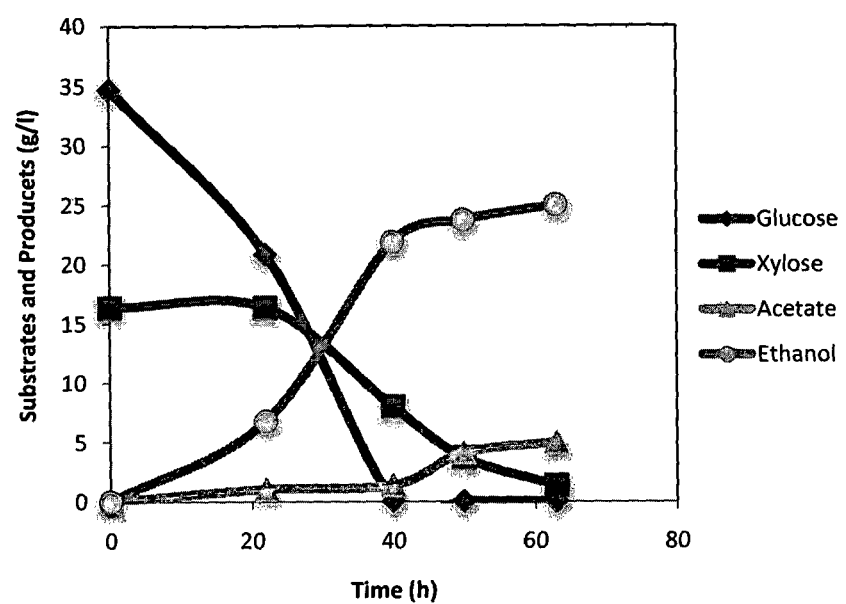
FIG. 11 is a graph showing the fermentation profile of SSY10 with ammonia treated hydrolysate at pH 7.0 in LB media with microaerobic conditions.

Fermentation of Sugars in Biomass Hydrolyzate Using SSY10 Strain:

Alkali (ammonia) treated biomass was prepared. Size reduced rice straw (average 5 mm length; 3.5 g) was mixed with 100 ml of 30% v/v liquid ammonia in water, at 15° C. The resultant rice straw-ammonia slurry was charged into a high pressure reactor. The reaction was carried out in the reactor vessel at 125° C. for 30 minutes to obtain first slurry. Temperature of the first slurry was reduced to at least 95° C. and subsequently the slurry was filtered to obtain a first filtrate comprising lignin and a first residue comprising cellulose and hemicellulose. The first residue comprising cellulose and hemicellulose was subjected to enzyme hydrolysis for recovery of C5 and C6 sugars. The biomass was further hydrolysed using the cellulolytic enzymes according to 100 pfu/g of dry weight for 4 hours at 50° C. by slow addition of biomass and was kept overnight at the same conditions. Once the sugars were extracted, the solution was pelleted at 5000 rpm for 20 min. The supernatant was transferred to a fresh bottle and was heat inactivated at 100° C. for 20 min and chilled immediately by placing it on ice. This helped to denature and precipitate the cellulase enzyme which was then separated by centrifugation at 8000 rpm for 20 min. The pH of the supernatant was set to 7.0, filter sterilized and stored at 4° C. SSY10 was used for fermenting ammonia treated biomass hydrolysate in LB broth at pH 6.8 under microaerobic conditions. A total of 50 g/l sugars were added in the fermentor with glucose being 34 g/l and xylose being 16 g/l. The engineered strain consumed all of the sugars, 34 g/l glucose and 16 g/l xylose, in 63 hours and produced 19.46 g/l of ethanol with maximum ethanol productivity of 0.85 g/l/h and yield of 0.4 g/g (FIG. 11). The acetate levels were marginally increased towards the end of fermentation. Thus it was shown that the engineered strain SSY10 could ferment the sugars in the hydrolysate very efficiently with excellent ethanol yield.

The modified E. coli strain SSY10 as per the present invention shows 68-83% theoretical ethanol yield. The modified E. coli strain SSY10 as per the present invention shows 95% theoretical ethanol yield when glucose was used as carbon source and shows 85-97% of the maximum theoretical ethanol yield when introduced in a microaerobic condition.

Although preferred embodiments of the invention are described herein in detail, it will be understood by those skilled in the art that variations may be made thereto without departing from the spirit of the invention or the scope of the appended claims.

The invention claimed is:

1. A modified *E. coli* strain capable of fermenting both hexose and pentose sugars for production of bioalcohol wherein a promoter of pyruvate dehydrogenase operon (PDH) is replaced with the promoter of a gene gapA.

2. The modified strain as claimed in claim 1, wherein the genes responsible for competing products selected from the consisting of lactate, succinate, acetate and formate are deleted.

3. The modified strain as claimed in claim 1, wherein basal level expression of one or more genes of the competing product is reintroduced.

4. The modified strain as claimed in claim 2, wherein the gene deleted for competing product lactate is Lactate dehydrogenase (IdhA).

5. The modified strain as claimed in claim 2, wherein the gene deleted for competing product acetate is Phosphotransacetylase (pta) or Acetate kinase (ack).

6. The modified strain as claimed in claim 2, wherein the gene deleted for competing product succinate is selected from Fumarate Reductase A (frdA), Fumarate Reductase B (frdB), Fumarate Reductase C (frdC), Fumarate Reductase D (frdD), Succinyl coA synthetase (SucC/SucD) or Isocitrate lyase (aceA).

7. The modified strain as claimed in claim 2, wherein the gene deleted for competing product formate is selected from Pyruvate formate lyase A (pflA) Pyruvate formate lyase B (pflB), Pyruvate formate lyase C (pflC) or Pyruvate formate lyase D (pflD).

* * * * *